United States Patent
Morgan et al.

(10) Patent No.: US 6,666,877 B2
(45) Date of Patent: Dec. 23, 2003

(54) APPARATUS AND METHOD FOR SECURING SUTURE TO BONE

(75) Inventors: Daniel E. Morgan, Salem, MA (US); Paul V. Fenton, Jr., Marblehead, MA (US); Thomas N. Fenton, Ipswich, MA (US); Vincent P. Novak, Groton, MA (US)

(73) Assignee: Axya Medical, Inc., Beverly, MA (US)

( * ) Notice: Subject to any disclaimer, the term of this patent is extended or adjusted under 35 U.S.C. 154(b) by 18 days.

(21) Appl. No.: 09/952,280

(22) Filed: Sep. 12, 2001

(65) Prior Publication Data

US 2002/0052630 A1 May 2, 2002

Related U.S. Application Data

(60) Provisional application No. 60/231,859, filed on Sep. 12, 2000.

(51) Int. Cl.[7] .................................. A61B 17/04
(52) U.S. Cl. ...................... 606/232; 606/218
(58) Field of Search .................. 128/772; 604/282, 604/164; 606/159, 127, 128, 198, 191, 200, 232, 218; 411/378, 303, 384, 392, 400; 403/326, 327, 328; 623/13.11, 13.12, 13.13, 13.14

(56) References Cited

U.S. PATENT DOCUMENTS

| | | | |
|---|---|---|---|
| 4,011,602 A | * | 3/1977 | Rybicki et al. .......... 623/23.76 |
| 4,632,100 A | | 12/1986 | Somers et al. |
| 5,152,790 A | | 10/1992 | Rosenberg et al. |
| 5,156,616 A | | 10/1992 | Meadows et al. |
| 5,370,662 A | * | 12/1994 | Stone et al. ................. 606/232 |
| 5,499,885 A | * | 3/1996 | Chapman .................... 403/380 |
| 5,584,835 A | * | 12/1996 | Greenfield ................... 606/73 |
| 5,662,683 A | | 9/1997 | Kay |
| 5,702,388 A | * | 12/1997 | Jackson et al. ............... 606/54 |
| 5,766,250 A | * | 6/1998 | Chervitz et al. .............. 606/72 |
| 5,957,953 A | * | 9/1999 | DiPoto et al. .............. 606/232 |
| 5,964,783 A | | 10/1999 | Grafton et al. |
| 6,027,523 A | * | 2/2000 | Schmieding ................ 606/232 |
| 6,056,751 A | * | 5/2000 | Fenton, Jr. ................... 606/72 |

* cited by examiner

Primary Examiner—Michael J. Milano
Assistant Examiner—P Roberts
(74) Attorney, Agent, or Firm—McDermott, Will & Emery (57) ABSTRACT

A suture anchor for securing soft tissue to bone, including a body having opposing first and second ends, a longitudinal axis extending between the ends, an external threaded portion extending from the first end, and a bore extending from the second end towards the first end. The body also has a first pair of slots extending laterally outwardly from the bore and extending longitudinally to a predetermined first distance from the second end, and a second pair of slots extending laterally outwardly from the bore and extending longitudinally to a predetermined second distance from the second end. The anchor additionally includes an eyelet receivable within the first and the second pairs of slots of the body and having an opening for receiving a suture, and a spring biasing the eyelet into the bore.

26 Claims, 7 Drawing Sheets

APPARATUS AND METHOD FOR SECURING SUTURE TO BONE

CROSS-REFERENCE TO RELATED APPLICATIONS

The present application claims priority to provisional U.S. patent application Ser. No. 60/231,859, filed on Sep. 12, 2000, which is assigned to the assignee of the present application and incorporated herein by reference.

FIELD OF THE INVENTION

The present invention generally relates an apparatus and method for securing suture to bone, and more particularly, to suture anchors for securing soft tissue to bone.

BACKGROUND OF THE INVENTION

When soft tissue tears away from bone, reattachment becomes necessary. Various devices, including sutures alone, screws, staples, wedges, and plugs have been used in the past to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 4,632,100 discloses a cylindrical threaded suture anchor. The suture anchor of the '100 patent includes a drill bit at a leading end for boring a hole in a bone, followed by a flight of threads spaced from the drill bit for securing the anchor into the hole created by the drill bit. U.S. Pat. No. 5,370,662 discloses a suture anchor having a flight of threads which extend to the tip of the anchor. U.S. Pat. No. 5,156,616 discloses a similar suture anchor having an axial opening for holding a knotted piece of suture.

All of the above-noted suture anchors include structure for attaching the suture to the anchor. U.S. Pat. No. 4,632,100, for example, discloses and claims a press-fitted disc and knot structure which secures the suture to the anchor. In other suture anchors, such as those disclosed in U.S. Pat. No. 5,370,662, the suture is passed through an eyelet located on the proximal end of the anchor. U.S. Pat. No. 5,152,790 discloses a suture anchor with a rotatable ring for securing suture to the suture anchor.

The devices discussed above are fairly time consuming and complicated to fasten the soft tissue against the bone mass. It is also difficult for these devices to keep the soft tissue tightly attached to the bone mass during the body's healing process.

It would therefore be an advantage to provide a suture anchor that simplifies the operation process and effectively secures the soft tissue against the bone mass during the body's healing period. Preferably, the suture anchor will be provided with an eyelet that is movable with respect to the anchor in order to simplify the process of attaching a suture to the eyelet.

SUMMARY OF THE INVENTION

In response, the present invention provides suture anchor for securing soft tissue to bone, including a body having opposing first and second ends, a longitudinal axis extending between the ends, an external threaded portion extending from the first end, and a bore extending from the second end towards the first end. The body also has a first pair of slots extending laterally outwardly from the bore and extending longitudinally to a predetermined first distance from the second end, and a second pair of slots extending laterally outwardly from the bore and extending longitudinally to a predetermined second distance from the second end.

The anchor additionally includes an eyelet receivable within the first and the second pairs of slots of the body and having an opening for receiving a suture, and a spring biasing the eyelet into the bore.

According to one aspect of the present invention, the first distance is sized to maintain the opening of the eyelet at least partly out of the bore, and the second distance is sized to allow the spring to bias the eyelet further into the bore. According to another aspect, the second distance is sized to allow the spring to bias the entire eyelet into the bore.

According to an additional aspect, the spring comprises a tension spring disposed along the axis within the bore and having a first end attached to the body member and a second end attached to the eyelet. According to a further aspect, the tension spring is helical. According to still another aspect, the bore of the body includes a socket, and the spring includes a mooring extending from the first end of the spring and secured in the socket for rotation therein.

The present invention provides another suture anchor for securing soft tissue to bone. The anchor includes a body member having a first end and a second end, a central axis extending between the first and the second ends, an external threaded portion coaxial with the central axis extending from the first end, and a bore extending coaxial with the central axis from the second end to a socket adjacent the first end. The anchor also includes an insert having a mooring secured in the socket, a shaft extending within the bore from the mooring towards the second end of the body member, and an eyelet secured to the shaft and having an opening for receiving a suture.

According to one aspect, the insert can be rotated with respect to the body member. According to another aspect, the insert can be moved vertically with respect to the body member.

These and other features and advantages of the present invention will be more fully appreciated with reference to the following detailed description which is to be read in conjunction with attached drawings.

BRIEF DESCRIPTION OF THE DRAWINGS

Like reference characters designate identical or corresponding components and units throughout the several views.

DETAILED DESCRIPTION OF THE PREFERRED EMBODIMENTS

Figure 1:
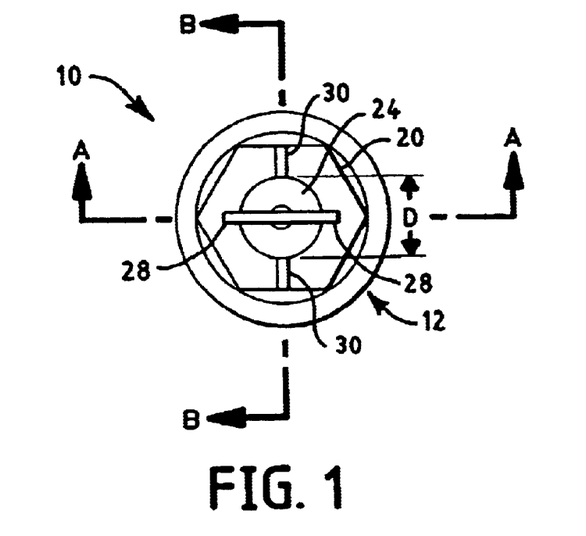
FIG. 1 is a top plan view of one embodiment of a suture anchor constructed in accordance with the present invention.
Figure 2:
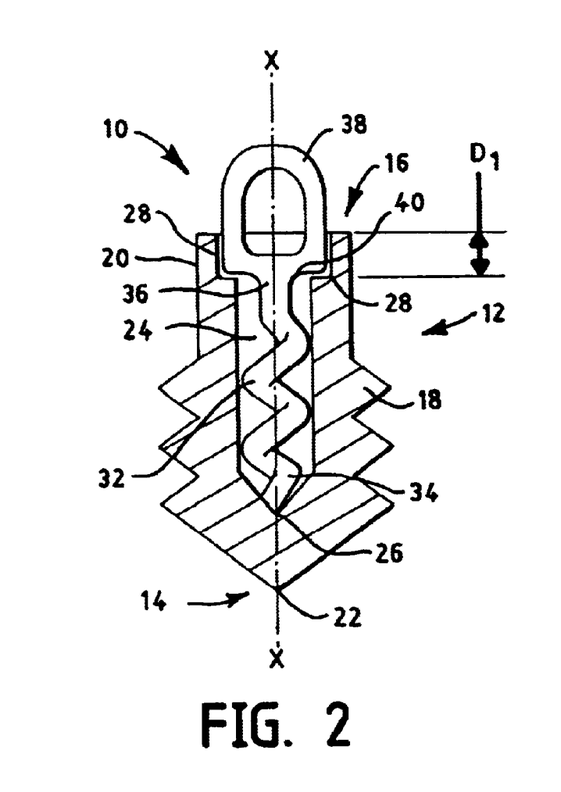
FIG. 2 is a sectional view of the suture anchor taken along line A—A of FIG. 1 showing an eyelet of the anchor in a maintained position.

The suture anchor of the present invention primarily is for use for securing soft tissue to bone in orthopedic surgery, though such anchors may be used in other fields as appropriate. Generally, as illustrated in FIGS. 1 and 2, the inventive suture anchor 10 includes an elongated body 12 which extends along a longitudinal axis X between a first end 14 and a second end 16. The elongated body 12 comprises an external threaded portion 18 extending from the first end 14 and a drive head portion 20 at the second end 16. The external threaded portion 18 is preferably self-tapping which includes a cutting edge (not shown).

As shown in FIG. 2, the tip 22 of the external threaded portion 18 may taper to a point or may be blunt-ended depending upon the specific environment in which the suture anchor 10 will be used. The external threaded portion 18 may also be self-drilling threads which can be formed and inserted directly into a bone by engaging the suture anchor 10 with a driver without previous formation of a hole. FIG. 1 shows the top view of the suture anchor 10 with a hexagonal drive head 20 that can be mated with a external drive tool (not shown) with a hexagonally-shaped cavity for receiving the drive head portion 20. Various other means for cooperating with an external drive tool may also be provided. For example, an octagonal drive head could be provided to mate with a drive tool with an octagonal cavity, and grooves could be provided to mate with a drive tool with flanges.

The elongated body 12 of FIGS. 1 and 2 also includes a central longitudinal bore 24 extending from the second end 16 to a base 26 within the elongated body 12. The bore 24 has a maximum dimension D transverse to the longitudinal axis X. Referring to FIG. 1, the central longitudinal bore 24 includes two pairs of slots. The first pair of slots 28 is formed on opposite sides of the central longitudinal bore 24 extending laterally outwardly from the bore 24 and extending longitudinally from the second end 16 to a distance $D_1$ from the second end 16, as shown in FIG. 2. The second pair of slots 30 is also formed on opposite sides of the bore 24, and preferably, as shown in FIG. 1, perpendicular with the first pair of slots 28. The second pair of slots 30 extends laterally outwardly from the central longitudinal bore 24 and longitudinally from the second end 16 to a distance $D_2$ from the second end 16, as shown in FIGS. 3 and 4.

The suture anchor 10 further includes a spring 32 disposed along the longitudinal axis X within the central longitudinal bore 24. Any spring that is suitable to implant into human body can be used. The maximum dimension D of the central longitudinal bore 24 is adapted to permit the spring to expand and contract within the central longitudinal bore 24. A first end 34 of the spring 32 is secured to the base 26 of the central longitudinal bore 24 preferably by ultrasonic welding. A second end 36 of the spring 32 is attached with an eyelet 38 having an opening for receiving sutures. The eyelet 38 is preferably molded integrally with the spring 32. The eyelet 38 has a support portion 40 facing the base 26 of the central longitudinal bore 24. The two pairs of slots 28 and 30 are sized to receive the support portion 40.

Figure 3:
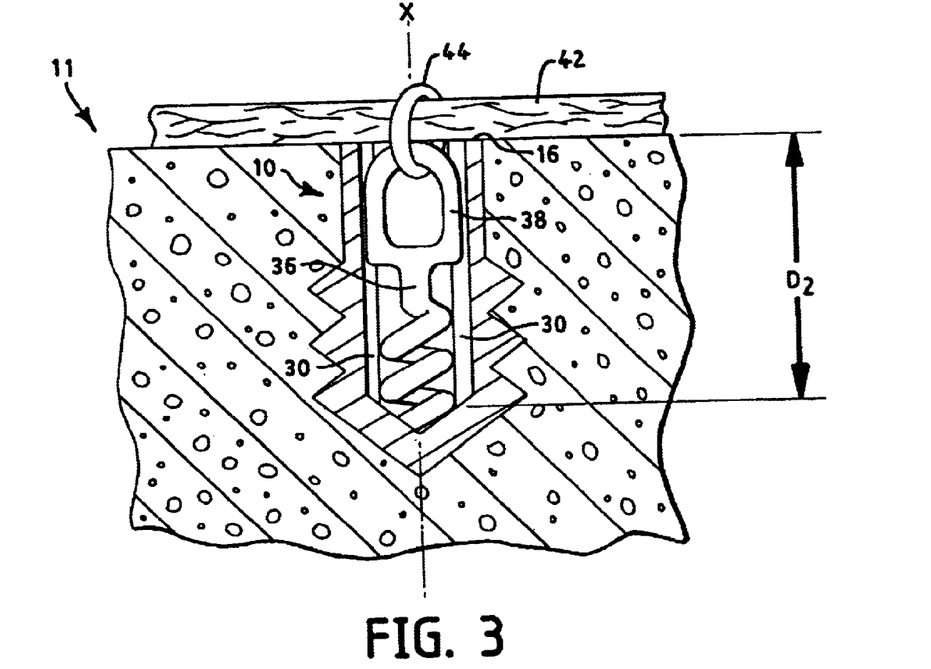
FIG. 3 is a sectional view of the suture anchor taken along line B—B of FIG. 1, after the eyelet has received a suture loop extending around a portion of soft tissue, and after rotation of the eyelet to a released position so that a spring of the anchor can begin to pull the eyelet further into the anchor.
Figure 4:
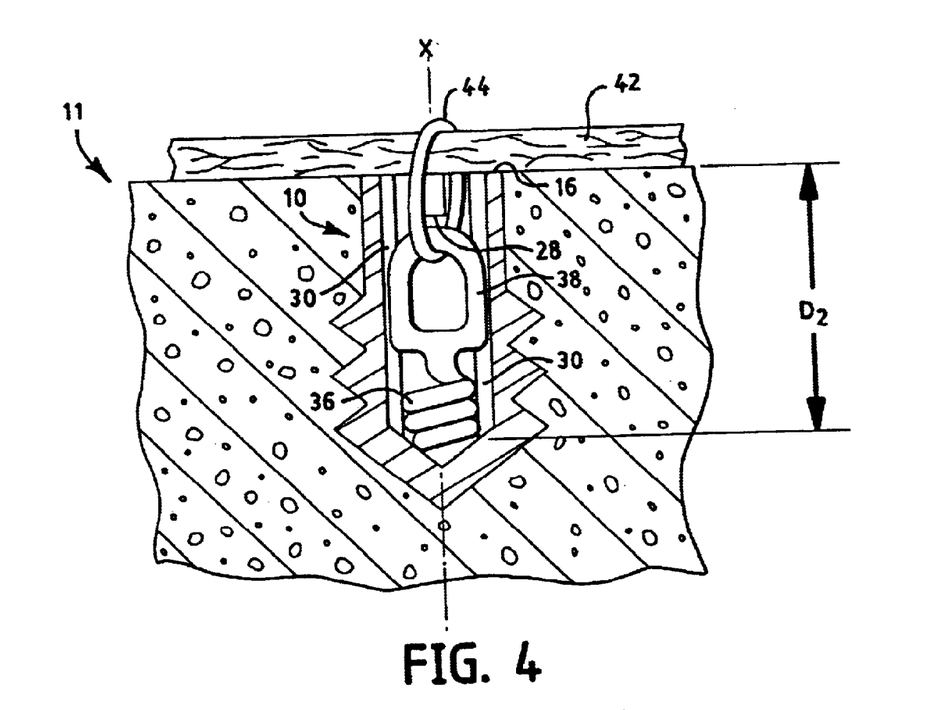
FIG. 4 is a sectional view of the suture anchor taken along line B—B of FIG. 1 after the spring of the anchor has pulled the eyelet fully into the anchor.

Referring to FIGS. 2 through 4, the exact length of $D_1$ and $D_2$ depend on such variables as the length of the central longitudinal bore 24, the length of the spring 32 and the size of the eyelet 38. Preferably, $D_1$ is short enough to keep the eyelet 38 proximally out of the central longitudinal bore 24, so that the sutures received by the eyelet 38 can be replaced or repositioned as needed during a surgical procedure without removing the suture anchor 10. In the preferred embodiment illustrated in FIGS. 3 and 4, the second pair of slots 30 extends through the central longitudinal bore 24 and $D_2$ equals the length of the central longitudinal bore 24. The second pair of slots 30, as shown in FIGS. 3 and 4, are adapted to permit longitudinal (along the X axis) sliding movement of the eyelet 38 within the slots 30.

Referring to FIGS. 3 and 4, the suture anchor 10 of the present invention secures a soft tissue 42 through a suture threaded through the eyelet 38 and formed into a suture loop 44. During a surgical operation, once the suture anchor 10 has been screwed into position, in bone 11 for example, the suture loop 44 is pulled (against the force of the spring 32) up within the second pair of slots 30, rotated, and positioned in the first pair of slots 28 (if not positioned in the first slots 28 prior to being screwed into the bone 11). The soft tissue 42 is then secured with the suture loop 44 through the accessible eyelet 38.

Once the soft tissue 42 is secured to the eyelet 38, the eyelet is pulled up and out of the first pair of slots 28, rotated (about axis X), until the support portion 40 of the eyelet is aligned over the second pair of slots 30, and released. The spring 32 then draws the released eyelet 38 longitudinally along the second pair of slots 30 towards the first end 14 of the anchor 10 to further secure the soft tissue 42 to the bone, as shown in FIG. 4.

In the embodiment of the suture anchor 10 shown in FIGS. 1–4, the spring comprises a helical tension spring 32. However, other types of springs can alternatively be used for biasing the eyelet 38 into the anchor 10. For example, the spring can comprise a simple elastic band or strip of elastically resilient material. The spring can also comprise a helical compression spring, for example, arranged within the body 12 to bias the eyelet 38 into the anchor 10.

Figure 5:
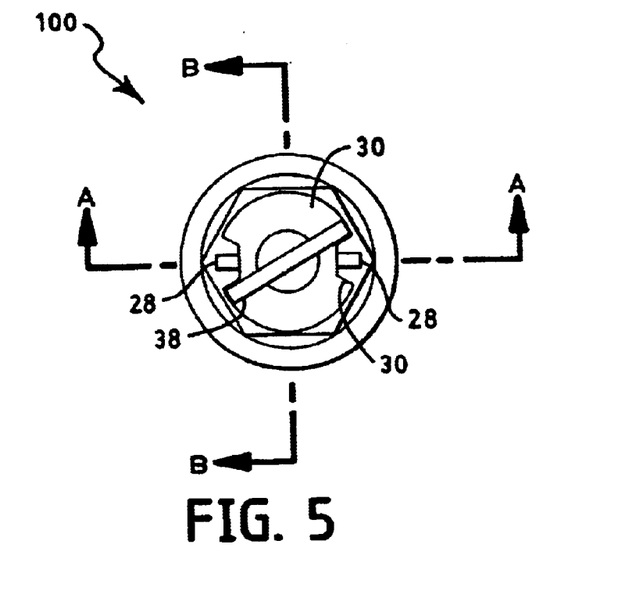
FIG. 5 is a top plan view of another embodiment of a suture anchor constructed in accordance with the present invention.

FIG. 5 is a top plan view of another preferred embodiment of a suture anchor 100 constructed in accordance with the present invention. As shown, the anchor 100 includes a second pair of slots 30 wide enough to allow the eyelet 38 to partially rotate within the slots 30 about the axis X. Preferably, the second pair of slots 30 is about one hundred and twenty degrees (120°) wide.

Figure 6:
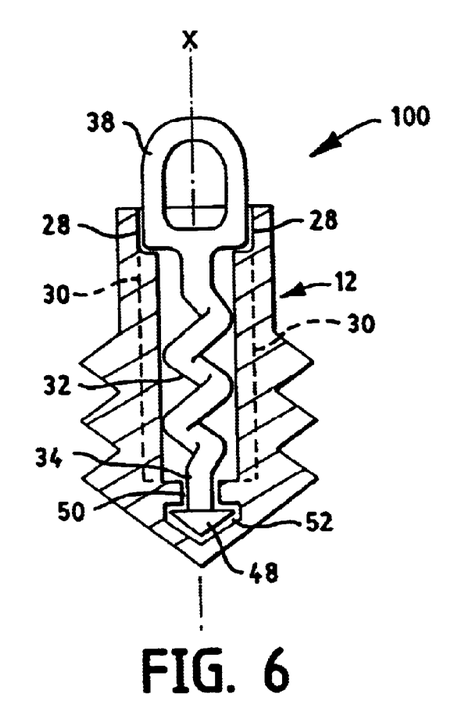
FIG. 6 is a sectional view of the suture anchor taken along line A—A of FIG. 5 showing an eyelet of the anchor in a maintained position.
Figure 7:
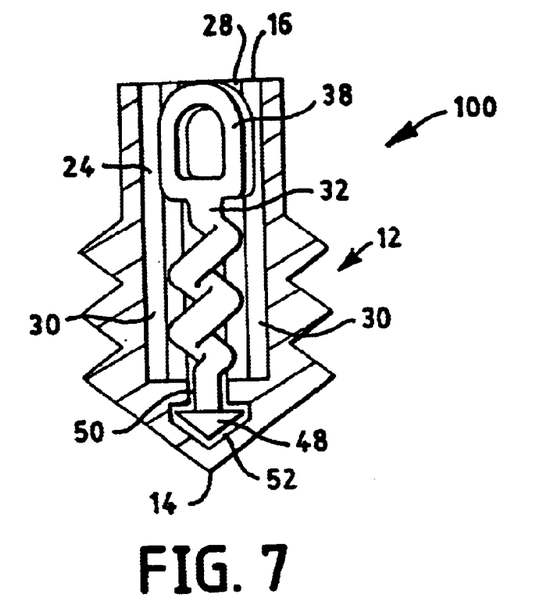
FIG. 7 is a sectional view of the suture anchor taken along line B—B of FIG. 5 after rotation of the eyelet to a released position so that a spring of the anchor can pull the eyelet into the anchor.
Figure 8:
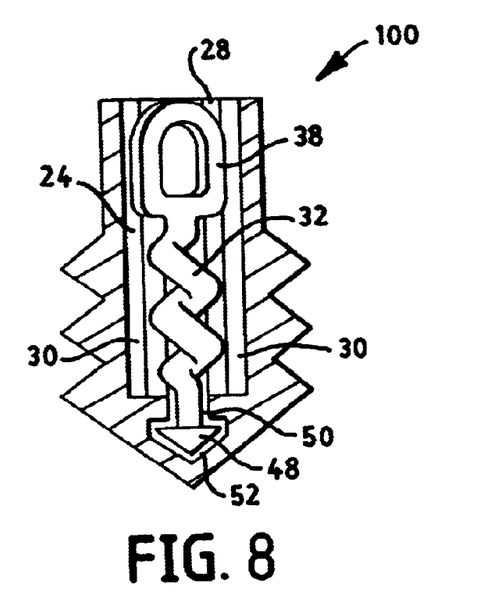
FIG. 8 is a sectional view of the suture anchor taken along line B—B of FIG. 5 after further rotation of the eyelet.

Referring to FIG. 6, the spring 32 is provided with a mooring 48 extending from the first end 34 of the spring. Preferably, the mooring 48 is molded integrally with the spring 32. The central longitudinal bore 24 further defines a neck portion 50 and a socket 52 at the base 26. The socket 52 is a cavity, which is sized to receive the mooring 48 of the spring 32 and permit the mooring 48 to rotate about the longitudinal axis X within the socket 52. The inner diameter of the neck portion 50 is sized to secure the mooring 48 within the socket 52. When turning the eyelet 38 into the second pair of slots 30, the eyelet 38 and the spring 32 can rotate about the longitudinal axis X within the central bore 24. FIGS. 7 and 8 show the spring 32 and the eyelet 38 being partially and fully rotated within the second pair of slots 30.

Figure 9:
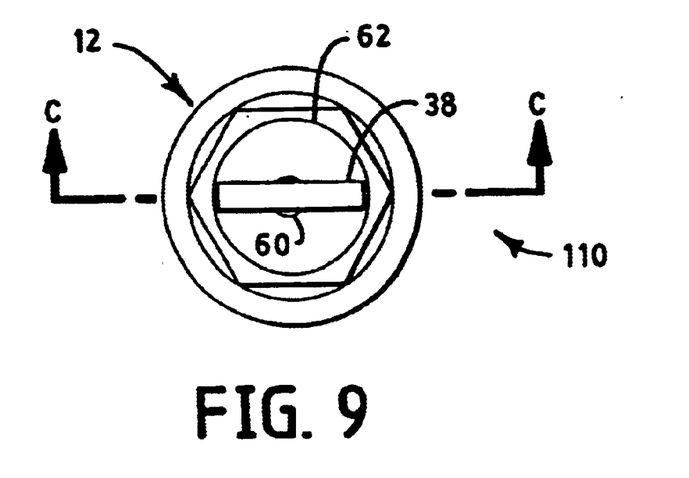
FIG. 9 is a top plan view of an additional embodiment of a suture anchor constructed in accordance with the present invention.
Figure 10:
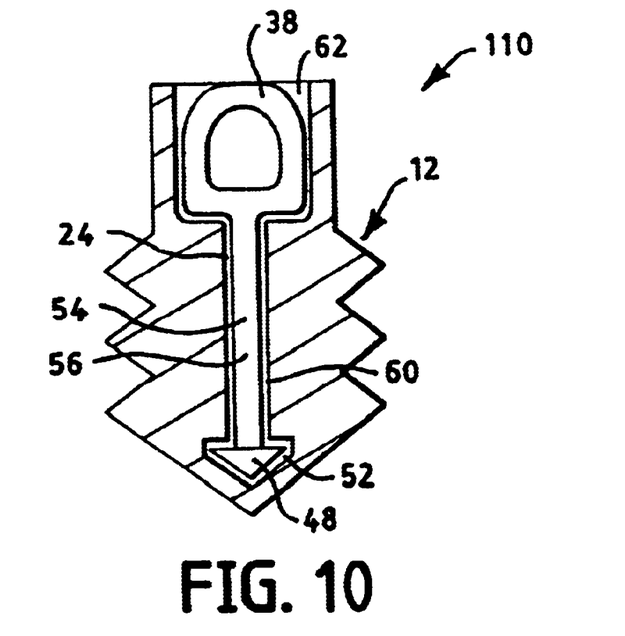
FIG. 10 is a sectional view of the suture anchor taken along line C—C of FIG. 9 showing an eyelet of the anchor rotatable about an axis of the anchor.

FIGS. 9 and 10 illustrate still another embodiment of the present invention, in which the suture anchor 110 includes an insert 54 having an eyelet 38 and a mooring 48 connected by a shaft 56. The central longitudinal bore 24 includes a socket 52 at the base 26 for rotatably receiving the mooring 48, a central portion 60, and an opening 62 at the second end 16 of the elongated body 12. The inner diameter of the central portion 60 is sized sufficiently small to secure the mooring 48 within the socket 52. The opening 62 is sized to hold the eyelet 38.

Figure 11:
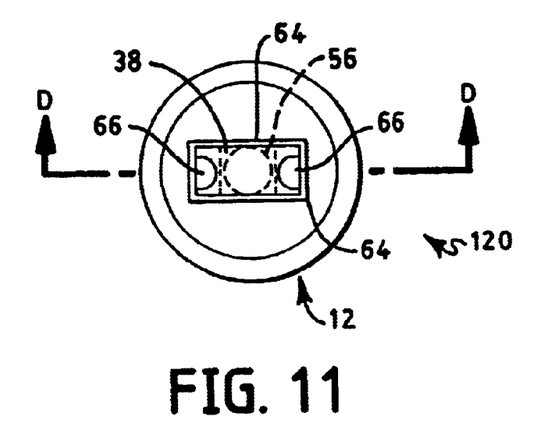
FIG. 11 is a top plan view of a embodiment of a suture anchor constructed in accordance with the present invention.
Figure 12:
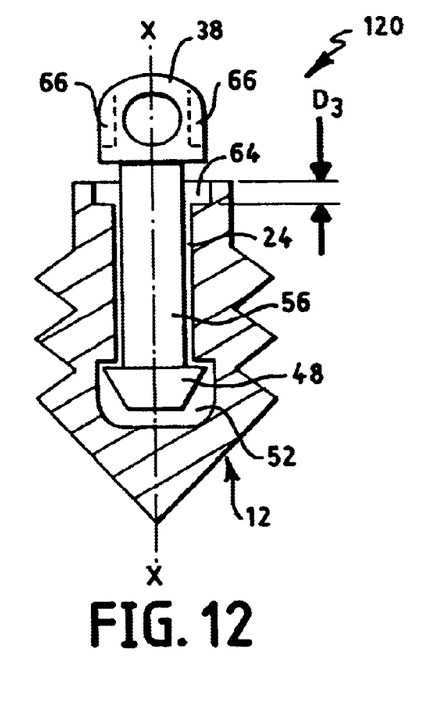
FIG. 12 is a sectional view of the suture anchor taken along line D—D of FIG. 11 showing an eyelet of the anchor rotatable about an axis of the anchor and movable about the axis.
Figure 13:
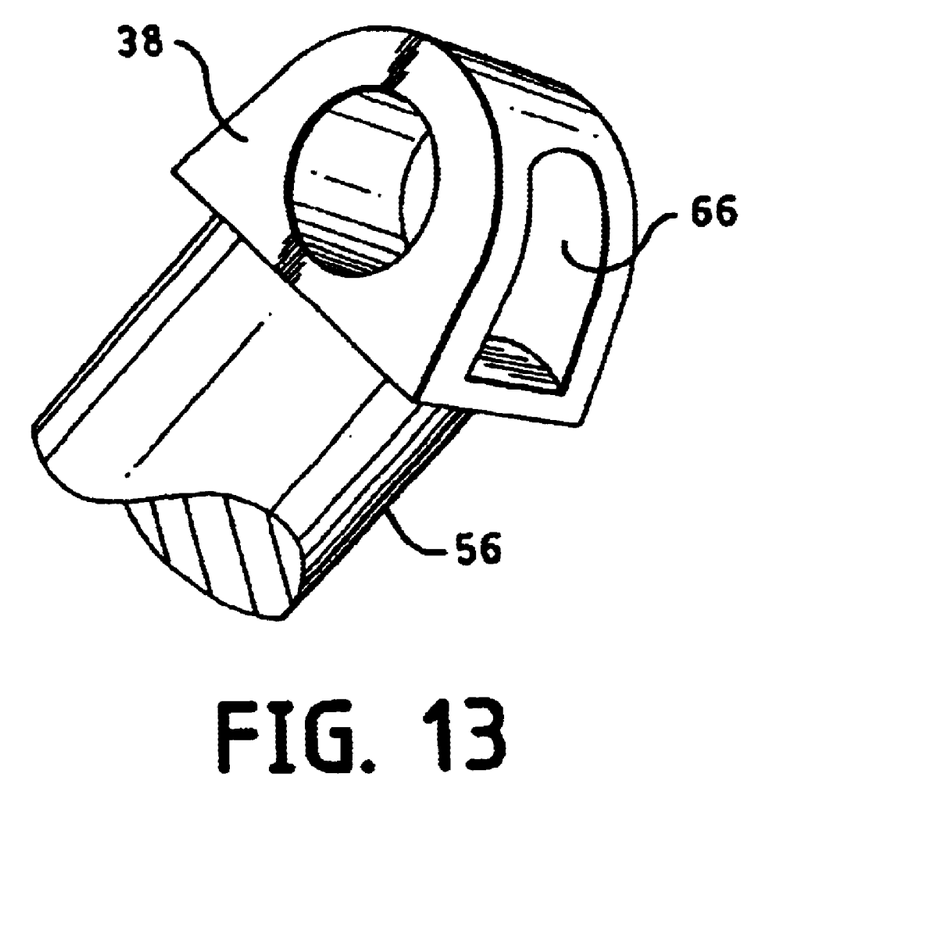
FIG. 13 is a perspective view of the eyelet of the suture anchor of FIG. 11.

In yet another embodiment, as shown in FIGS. 11 and 12, the suture anchor 120 includes a central longitudinal bore 24 having a pair of slots 64, which extend laterally outwardly from the opposite sides of the bore 24 and longitudinally from the second end 16 to a distance $D_3$ from the second end 16. Preferably, $D_3$ is short enough to keep the eyelet 38 proximally out of the central longitudinal bore 24. The pair of slots 64 is adapted to receive and secure the eyelet 38 such that the eyelet can not be rotated with respect to the body 12. As shown is FIG. 13, the eyelet 38 further includes a pair of driver recesses 66 formed on the opposite sides of the eyelet 38. The driver recesses 66 can be used to receive a drive tool for driving the anchor into bone.

Referring to FIG. 12, the socket 52 extends sufficiently deep to permit the mooring 48 to move longitudinally within the socket. In the up position, as shown in FIG. 12, the eyelet 38 is pulled out of the slots 64 and can be rotated about the longitudinal axis X. In the down position, the eyelet 38 is secured in the slots 64, and can be used to drive the anchor into bone by engaging a drive tool to the driver recesses 66 of the eyelet 38.

The suture anchor, which includes the elongated body, the spring, the eyelet, and the mooring and the shaft in some embodiments, may be manufactured from stainless steel, titanium, or some other durable, non-degradable, biocompatible material. Alternatively and preferably, the suture anchor can be made of a bioresorbable material which will be resorbed after residing in a patient.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of he equivalency of the claims are therefore intended to be embraced therein.

What is claimed is:

1. A suture anchor for securing soft tissue to bone, comprising:
    A) a body extending along a longitudinal axis between opposing first and second ends and having,
        an external threaded portion extending coaxial with the axis,
        a bore extending from the second end towards the first end,
        a first pair of slots extending laterally outwardly from the bore and extending longitudinally to a predetermined first distance from the second end, and
        a second pair of slots extending radially outwardly from the bore and extending longitudinally to a predetermined second distance from the second end; and
    B) an eyelet receivable within the first and the second pairs of slots of the body and having an opening for receiving a suture; and
    C) a spring biasing the eyelet into the bore.

2. A suture anchor according to claim 1, wherein the second distance is greater than the first distance.

3. A suture anchor according to claim 2, wherein the first distance is sized to maintain the opening of the eyelet at least partly out of the bore, and wherein the second distance is sized to allow the spring to bias the eyelet further into the bore along the axis.

4. A suture anchor according to claim 3, wherein the second distance is sized to allow the spring to bias the entire eyelet into the bore.

5. A suture anchor according to claim 4, wherein the second distance substantially equals a length of the bore.

6. A suture anchor according to claim 1, wherein the first pair of slots and the second pair of slots are perpendicular.

7. A suture anchor according to claim 1, wherein the second pair of slots is wider than the first pair of slots.

8. A suture anchor according to claim 7, wherein the second pair of slots has a width of about one hundred and twenty degrees (120°).

9. A suture anchor according to claim 1, wherein the spring comprises a tension spring disposed along the axis within the bore and having a first end attached to the body and a second end attached to the eyelet.

10. A suture anchor according to claim 9, wherein the tension spring is helical.

11. A suture anchor according to claim 9, wherein the first end of the spring extends from a base of the bore and is unitarily formed with the body.

12. A suture anchor according to claim 9, wherein:
    the bore includes a socket; and
    the spring includes a mooring extending from the first end of the spring and secured in the socket.

13. A suture anchor according to claim 12, wherein the mooring is rotatably secured in the socket.

14. A suture anchor according to claim 1, wherein the body further includes a drive head at the second end.

15. A suture anchor according to claim 14, wherein the drive head has a hexagonal engagement surface facing laterally outwardly from the axis.

16. A suture anchor according to claim 1, wherein the external threaded portion includes a self-tapping tip at the first end of the body.

17. A suture anchor according to claim 1, wherein the external threaded portion includes a self-drilling tip at the first end of the body.

18. A suture anchor for securing soft tissue to bone, comprising:
    A) a body extending along a longitudinal axis between opposing first and second ends and having,
        an external threaded portion extending coaxial with the axis,
        a bore longitudinally extending from the second end to a socket adjacent the first end; and
    B) an insert including,
        a mooring secured in the socket,
        a shaft extending within the bore from the mooring towards the second end of the body, and
        an eyelet secured to the shaft and having an opening for receiving a suture, wherein the eyelet has recesses for mating with a drive tool.

19. A suture anchor according to claim 18, wherein the insert is formed as a unitary piece.

20. A suture anchor according to claim 18, wherein the insert can be rotated with respect to the body.

21. A suture anchor according to claim 18, wherein the insert can be moved vertically with respect to the body.

22. A suture anchor according to claim 18, wherein the body includes a pair of slots at the second end sized to receive the eyelet.

23. A suture anchor according to claim 18, wherein the body further includes a drive head at the second end.

24. A suture anchor according to claim 23, wherein the drive head has a hexagonal engagement surface facing laterally outwardly from the axis.

25. A suture anchor according to claim 18, wherein the external threaded portion includes a self-tapping tip at the first end of the body.

26. A suture anchor according to claim 18, wherein the external threaded portion includes a self-drilling tip at the first end of the body.

* * * * *